(12) United States Patent
Suddaby

(10) Patent No.: US 11,583,411 B2
(45) Date of Patent: Feb. 21, 2023

(54) EXPANDABLE INTERVERTEBRAL FUSION IMPLANT

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 0 days.

(21) Appl. No.: 17/081,003

(22) Filed: Oct. 27, 2020

(65) Prior Publication Data

US 2022/0125599 A1 Apr. 28, 2022

(51) Int. Cl.
*A61F 2/44* (2006.01)
*A61F 2/30* (2006.01)

(52) U.S. Cl.
CPC .......... *A61F 2/4455* (2013.01); *A61F 2/4425* (2013.01); *A61F 2002/30332* (2013.01); *A61F 2002/30433* (2013.01); *A61F 2002/443* (2013.01)

(58) Field of Classification Search
CPC ...... A61F 2/4455; A61F 2/4465; A61F 2/447; A61F 2/446; A61F 2002/30556; A61F 2002/30553; A61F 2002/30555; A61F 2002/30266; A61F 2002/30545; A61F 2002/30525; A61F 2002/30523
See application file for complete search history.

(56) References Cited

U.S. PATENT DOCUMENTS

| 3,922,726 | A * | 12/1975 | Trentani | ..................... | A61F 2/36 623/22.15 |
|---|---|---|---|---|---|
| 9,474,626 | B2 | 10/2016 | Jimenez et al. | | |
| 10,117,755 | B2 * | 11/2018 | Emerick | ................. | A61F 2/442 |
| 10,172,718 | B2 * | 1/2019 | Wolters | ............. | A61B 17/8858 |
| 11,207,192 | B2 * | 12/2021 | Suddaby | ................. | A61F 2/447 |
| 2003/0065396 | A1 * | 4/2003 | Michelson | ............. | A61F 2/447 623/17.11 |
| 2006/0149385 | A1 * | 7/2006 | McKay | ................. | A61F 2/4455 623/17.15 |
| 2007/0198089 | A1 | 8/2007 | Moskowitz et al. | | |
| 2008/0140207 | A1 * | 6/2008 | Olmos | .................... | A61F 2/447 623/17.11 |
| 2011/0172774 | A1 * | 7/2011 | Varela | .................... | A61F 2/447 623/17.16 |

(Continued)

FOREIGN PATENT DOCUMENTS

EP 2368529 A1 * 9/2011 ........... A61F 2/4465

*Primary Examiner* — Jan Christopher L Merene
(74) *Attorney, Agent, or Firm* — Harter Secrest & Emery LLP; Michael Nicholas Vranjes

(57) ABSTRACT

An expandable intervertebral fusion implant, including an inferior component, including a first top surface, a first bottom surface, a first end including a first worm rotatably arranged therein, and a second end including a second worm rotatable arranged therein, a superior component, including a second top surface, a second bottom surface, a third end, and a fourth end, and a first expansion mechanism including a first screw, the first screw including a first bottom end connected to the inferior component and a first top end connected to the superior component, wherein as the first worm is rotated in a first circumferential direction, the first screw rotates in a second circumferential direction and the superior component is displaced relative to the inferior component.

16 Claims, 13 Drawing Sheets

(56) References Cited

U.S. PATENT DOCUMENTS

| | | | |
|---|---|---|---|
| 2012/0109128 A1* | 5/2012 | Frigg | A61B 17/748 606/64 |
| 2012/0323329 A1* | 12/2012 | Jimenez | F16H 25/20 623/17.16 |
| 2013/0158668 A1* | 6/2013 | Nichols | A61F 2/4611 623/17.16 |
| 2013/0274883 A1* | 10/2013 | McLuen | A61F 2/28 623/17.16 |
| 2015/0094814 A1* | 4/2015 | Emerick | A61F 2/447 623/17.16 |
| 2017/0224505 A1 | 8/2017 | Butler et al. | |
| 2018/0071110 A1* | 3/2018 | Overes | A61F 2/4455 |
| 2019/0083279 A1 | 3/2019 | Suddaby | |
| 2020/0100905 A1 | 4/2020 | Sharifi-Mehr et al. | |
| 2020/0405499 A1* | 12/2020 | Gerbec | A61F 2/4425 |

\* cited by examiner

EXPANDABLE INTERVERTEBRAL FUSION IMPLANT

FIELD

The present disclosure relates to orthopedic surgery, and more particularly to an expandable and deployable intervertebral fusion implant capable of being placed within an intervertebral disc space and expanded.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, five in the lower back or lumbar region, and five in the pelvic or sacral region, which are normally fused together to form the back part of the pelvis. This column of bones is critical for providing structural support for the entire body.

Between the vertebral bones themselves exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal movement.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of stability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prosthesis in various forms has therefore been used to provide immediate stability and to protect and preserve an environment that fosters growth of the grafted bone such that a structurally significant bony fusion can occur.

Limitations of most present-day intervertebral implants are significant and revolve largely around the marked variation in the disc space height and shape that result from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2-3 mm must be added on either side resulting in a final implant size of 24-26 mm. During implantation from an anterior approach (i.e., from the front of the body), excessive retraction (or pulling) is often required on the great blood vessels, which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of distraction to obtain stability by tightening the annular ligamentous tension band. Compromising on implant size risks sub-optimal stability or a loose implant, which has a greater risk of migration within, or expulsion from, the disc space. The alternative of excessively retracting neural elements to facilitate a posterior implant application results in a neuropraxia at best and permanent neural damage at worst.

Thus, there is a long-felt need for an expandable and deployable intervertebral fusion implant capable of being placed within an intervertebral disc space and expanded.

SUMMARY

According to aspects illustrated herein, there is provided an expandable intervertebral fusion implant, comprising an inferior component, including a first top surface, a first bottom surface, a first end including a first worm rotatably arranged therein, and a second end including a second worm rotatable arranged therein, a superior component, including a second top surface, a second bottom surface, a third end, and a fourth end, and a first expansion mechanism including a first screw, the first screw comprising a first bottom end connected to the inferior component and a first top end connected to the superior component, wherein as the first worm is rotated in a first circumferential direction, the first screw rotates in a second circumferential direction and the superior component is displaced relative to the inferior component.

In some embodiments, the first worm comprises a radially outward facing surface comprising threading, and the first expansion mechanism further comprises a first bevel gear engaged with the threading. In some embodiments, the first expansion mechanism further comprises a first sleeve threadably engaged with the first worm. In some embodiments, as the first screw rotates in the second circumferential direction, the first sleeve displaces relative to the inferior component. In some embodiments, the first sleeve is pivotably connected to the superior component. In some embodiments, the superior component further comprises a frusto-conical hole extending from the second bottom surface, and the first sleeve engages the frusto-conical hole. In some embodiments, the second worm is spaced apart from the first worm. In some embodiments, the first worm comprises a through-hole. In some embodiments, the expandable intervertebral fusion implant further comprises a second expansion mechanism including a second screw, the second screw comprising a second bottom end connected to the inferior component and a second top end connected to the superior component. In some embodiments, as the second worm is rotated in the first circumferential direction, the second screw rotates in the second circumferential direction and the superior component is displaced relative to the inferior component. In some embodiments, the first worm and the second worm are concentrically aligned. In some embodiments, the expandable intervertebral fusion implant further comprises a section extending from one of the inferior component and the superior component and a groove arranged in the other of the inferior component and the superior component, the section being engaged with the groove.

According to aspects illustrated herein, there is provided an expandable intervertebral fusion implant, comprising an inferior component, including a first top surface, a first bottom surface, a first end including a first worm rotatably arranged therein, and a second end including a second worm rotatable arranged therein, a superior component, including a second top surface, a second bottom surface, a third end, and a fourth end, a first expansion mechanism including a first screw, the first screw comprising a first bottom end connected to the inferior component and a first top end connected to the superior component, and a second expansion mechanism including a second screw, the second screw comprising a second bottom end connected to the inferior component and a second top end connected to the superior component, wherein as the first worm is rotated in a first circumferential direction, the first screw rotates in a second circumferential direction and the superior component is displaced relative to the inferior component, and as the second worm is rotated in the first circumferential direction, the second screw rotates in the second circumferential direction and the superior component is displaced relative to the inferior component.

In some embodiments, the first worm comprises a radially outward facing surface comprising threading, and the first expansion mechanism further comprises a first bevel gear arranged at the first bottom end engaged with the threading. In some embodiments, the first expansion mechanism further comprises a first sleeve threadably engaged with the first worm, and as the first screw rotates in the second circumferential direction, the first sleeve displaces relative to the inferior component. In some embodiments, the first top end is pivotably connected to the superior component. In some embodiments, the superior component further comprises a frusto-conical hole extending from the second bottom surface, and the first screw engages the frusto-conical hole. In some embodiments, the second worm is spaced apart from the first worm, and the first worm and the second worm are concentrically aligned. In some embodiments, the first worm comprises a through-hole.

According to aspects illustrated herein, there is provided an expandable intervertebral fusion implant, comprising an inferior component, including a first top surface, a first bottom surface, a superior component, including a second top surface, a second bottom surface including a first frusto-conical hole and a second frusto-conical hole, a first worm including a through-hole, a second worm spaced apart from the first worm, a first expansion mechanism including a first screw engaged with the first worm and the first frusto-conical hole, the first screw comprising a first bottom end connected to the inferior component and a first top end pivotably connected to the superior component, and a second expansion mechanism including a second screw engaged with the second worm and the second frusto-conical hole, the second screw comprising a second bottom end connected to the inferior component and a second top end pivotably connected to the superior component, wherein as the first worm is rotated in a first circumferential direction, the first screw rotates in a second circumferential direction and the superior component is displaced away from the inferior component, and as the second worm is rotated in the first circumferential direction, the second screw rotates in the second circumferential direction and the superior component is displaced away from the inferior component.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Figure 1:
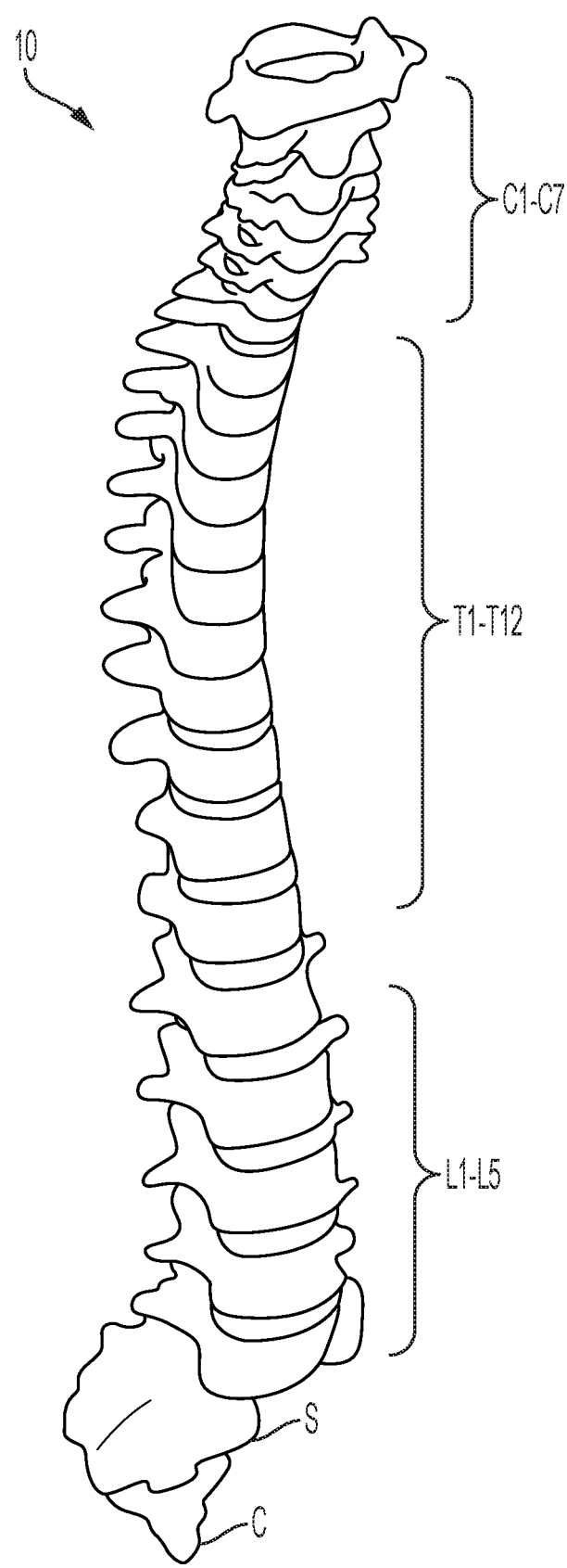
FIG. 1 is an anterior perspective view of a spinal column.
Figure 2:
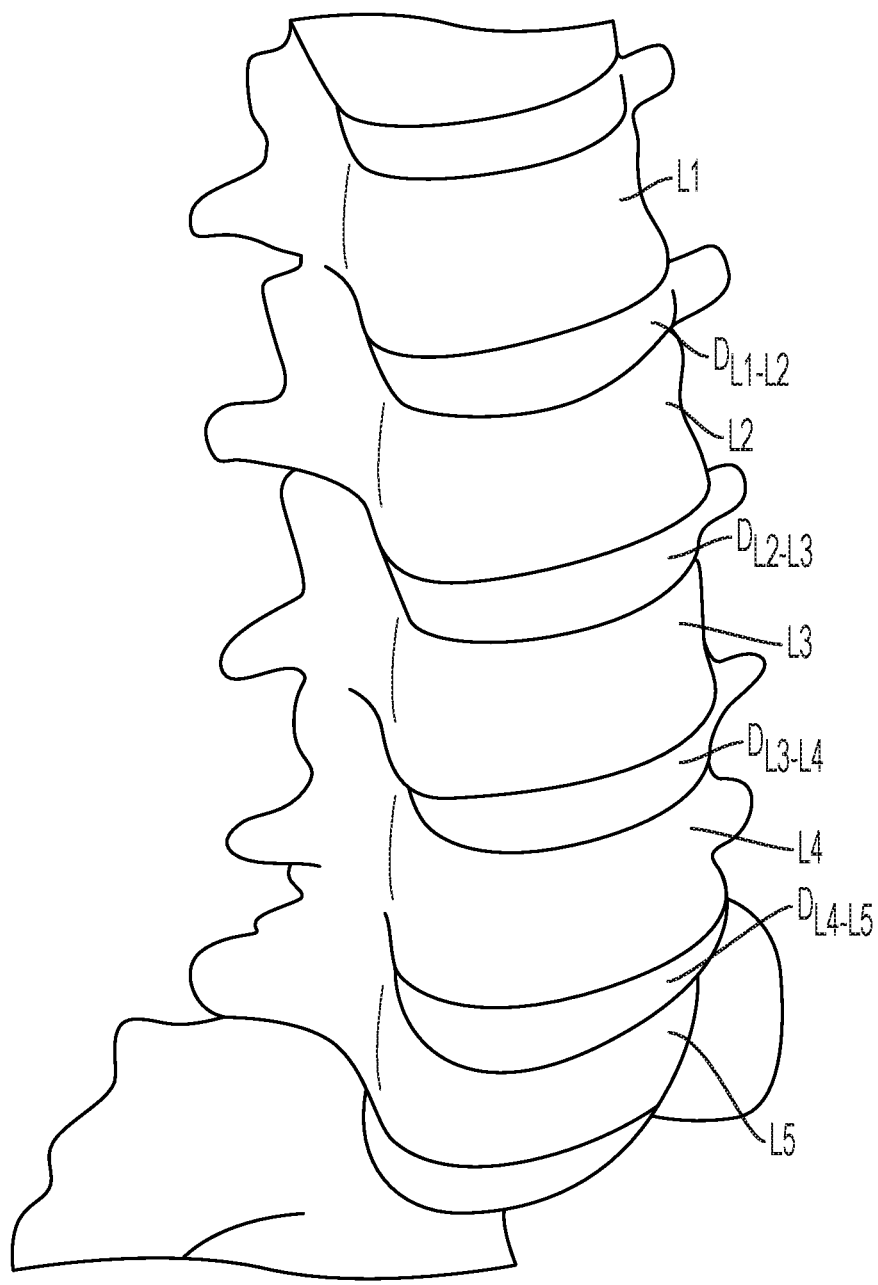
FIG. 2 is an anterior perspective view of the lumbar section of the spinal column shown in FIG. 1.
Figure 3:
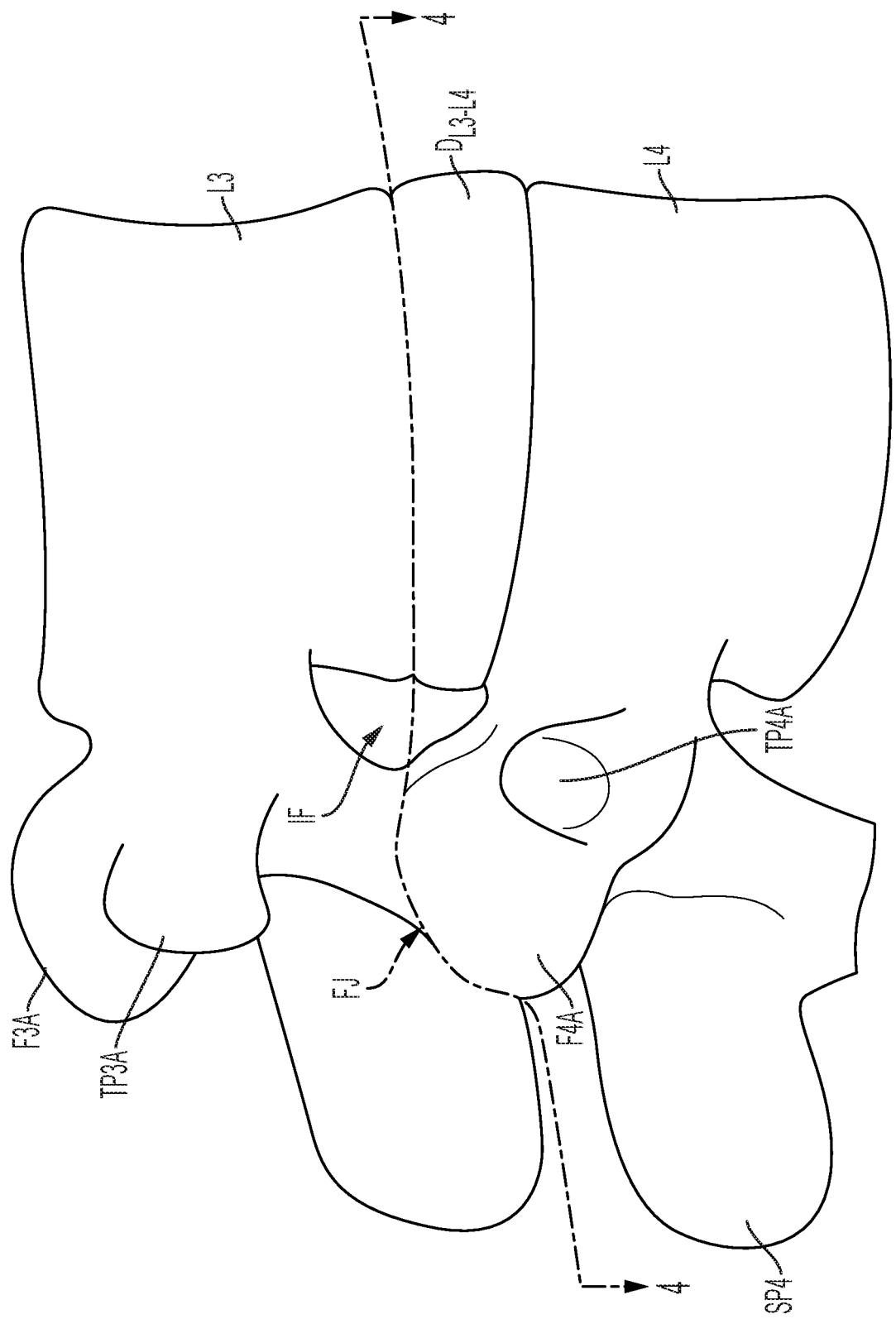
FIG. 3 is a lateral perspective view of two vertebrae, a disc, and related spinal anatomy.
Figure 4:
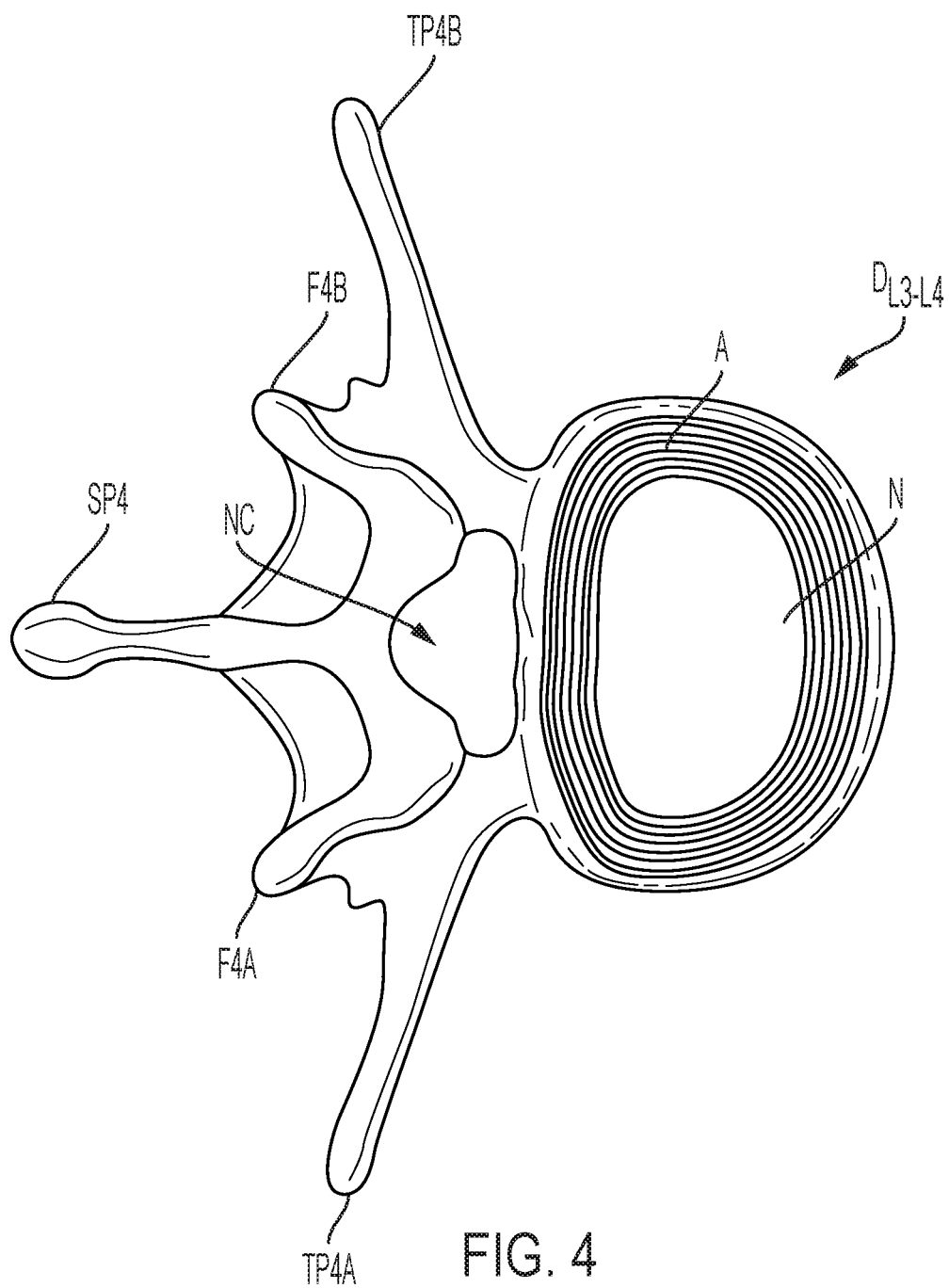
FIG. 4 is a top view of a section of the spinal column, taken generally along line 4-4 in FIG. 3.
Figure 5:
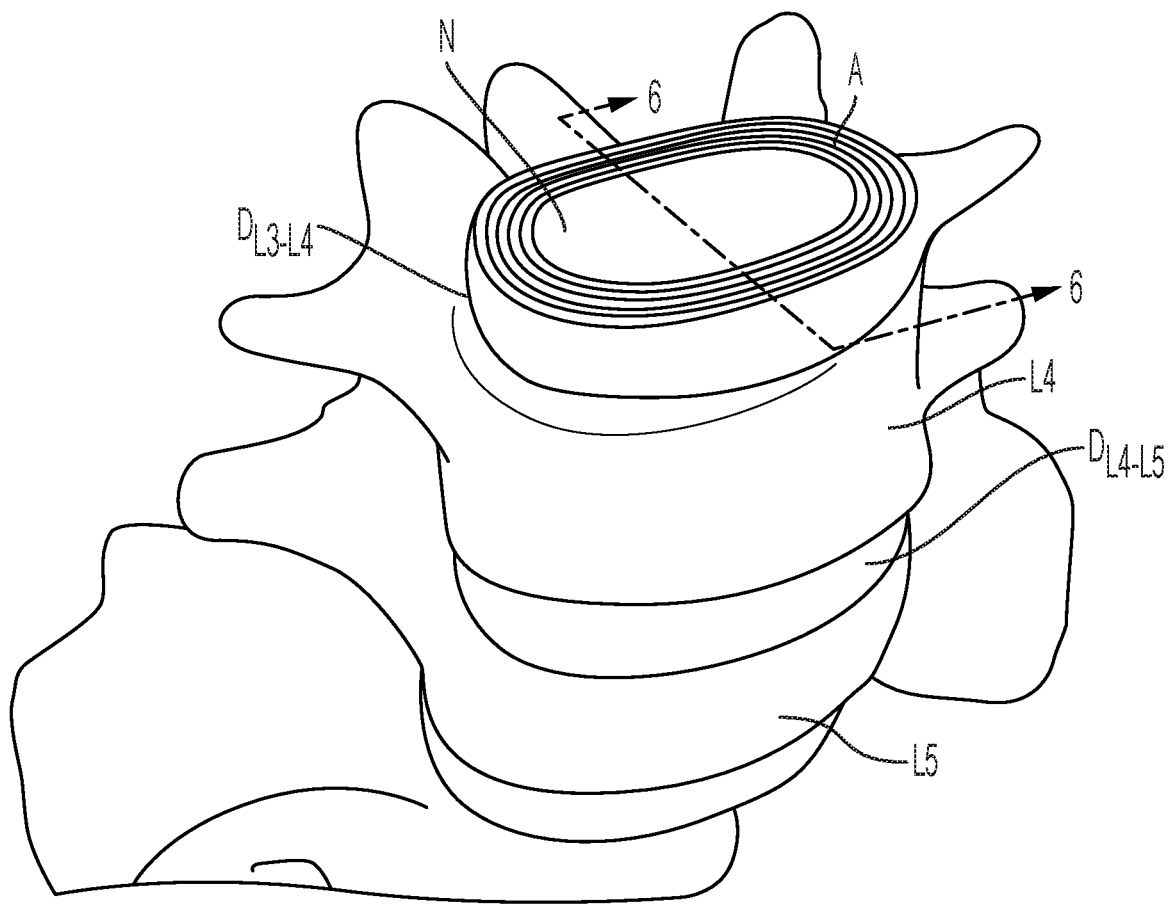
FIG. 5 is an enlarged anterior perspective view of the spinal column shown in FIG. 2, except with the top vertebra and all other structure above the top vertebra removed.
Figure 6:
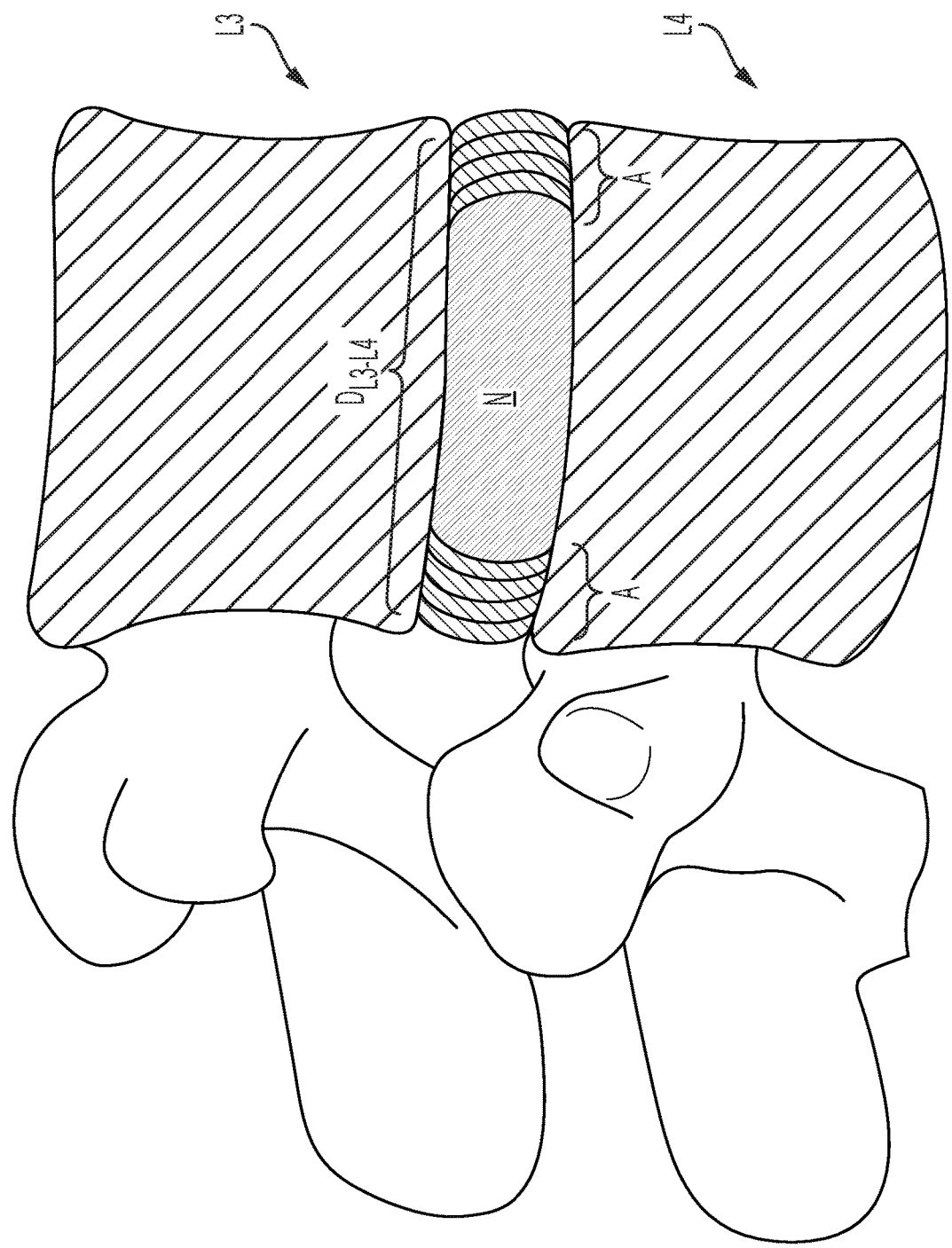
FIG. 6 is a partial cross-sectional view of the top and bottom vertebrae and disc, taken generally along line 6-6 in FIG. 5.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

By "non-rotatably connected" elements, we mean that: the elements are connected so that whenever one of the elements rotate, all the elements rotate; and, relative rotation between the elements is not possible. Radial and/or axial movement of non-rotatably connected elements with respect to each other is possible, but not required. By "rotatably connected" elements, we mean that: the elements are rotatable with respect to each other; and, whenever one element is displaced radially and/or axially, all the elements are displaced radially and/or axially.

Adverting now to the figures, and as described previously, FIGS. 1-6 depict various parts and sections of spinal anatomy.

Figure 7A:
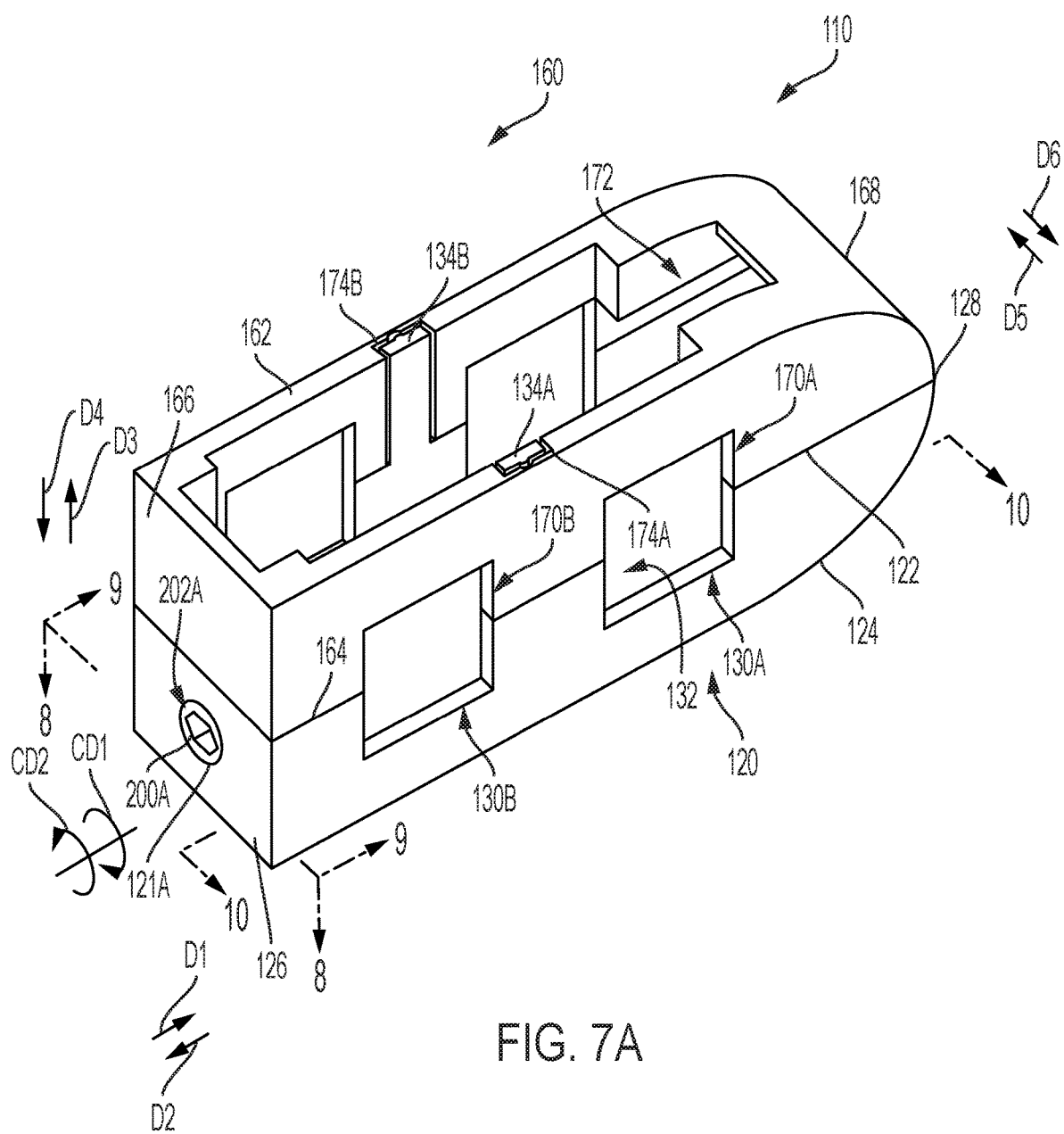
FIG. 7A is a front perspective view of an expandable intervertebral fusion implant, in a collapsed state.
Figure 7B:
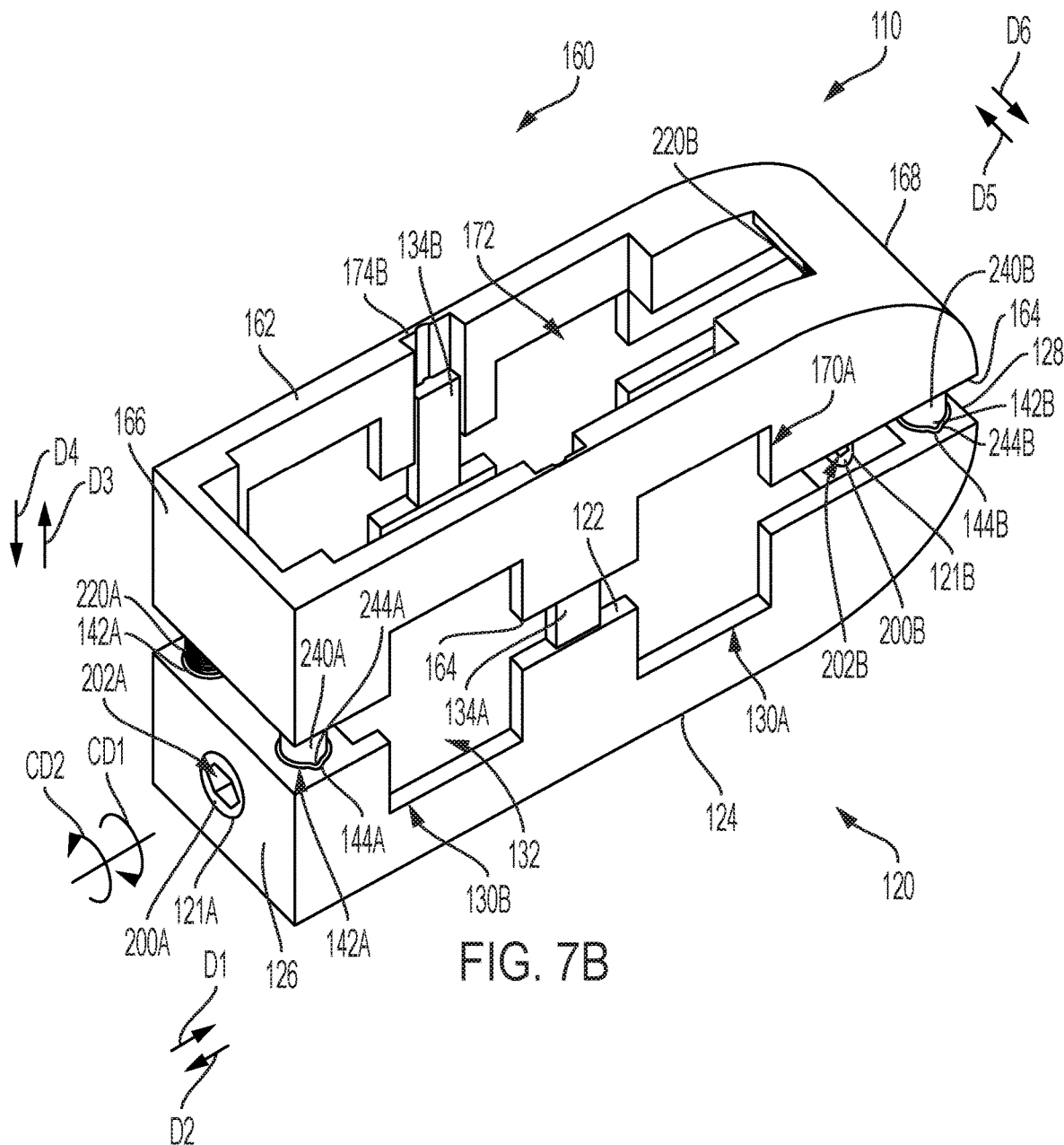
FIG. 7B is a front perspective view of the expandable intervertebral fusion implant shown in FIG. 7A, in an expanded state.
Figure 8:
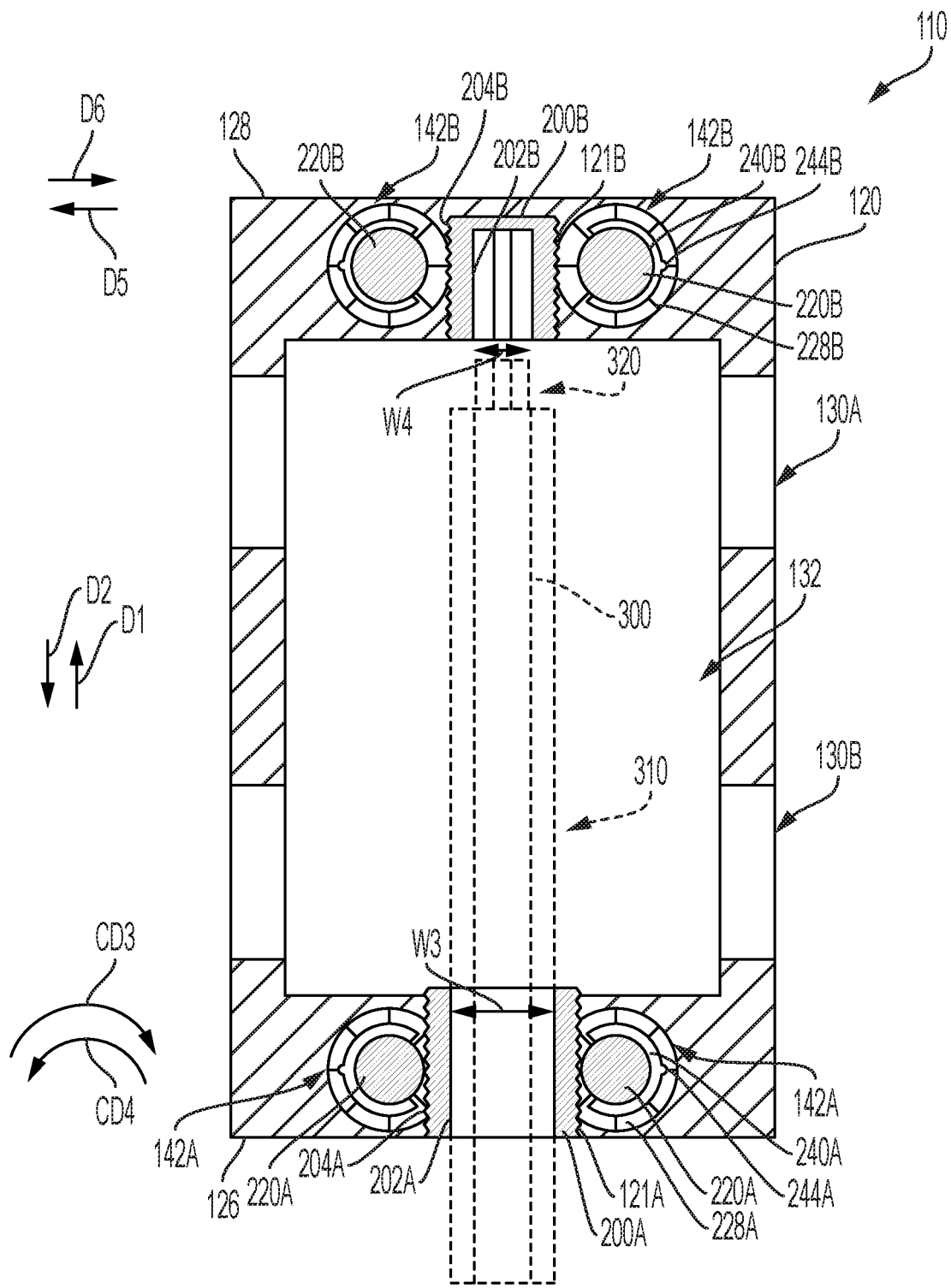
FIG. 8 is a cross-sectional view of the expandable intervertebral fusion implant taken generally along line 8-8 in FIG. 7A.
Figure 9:
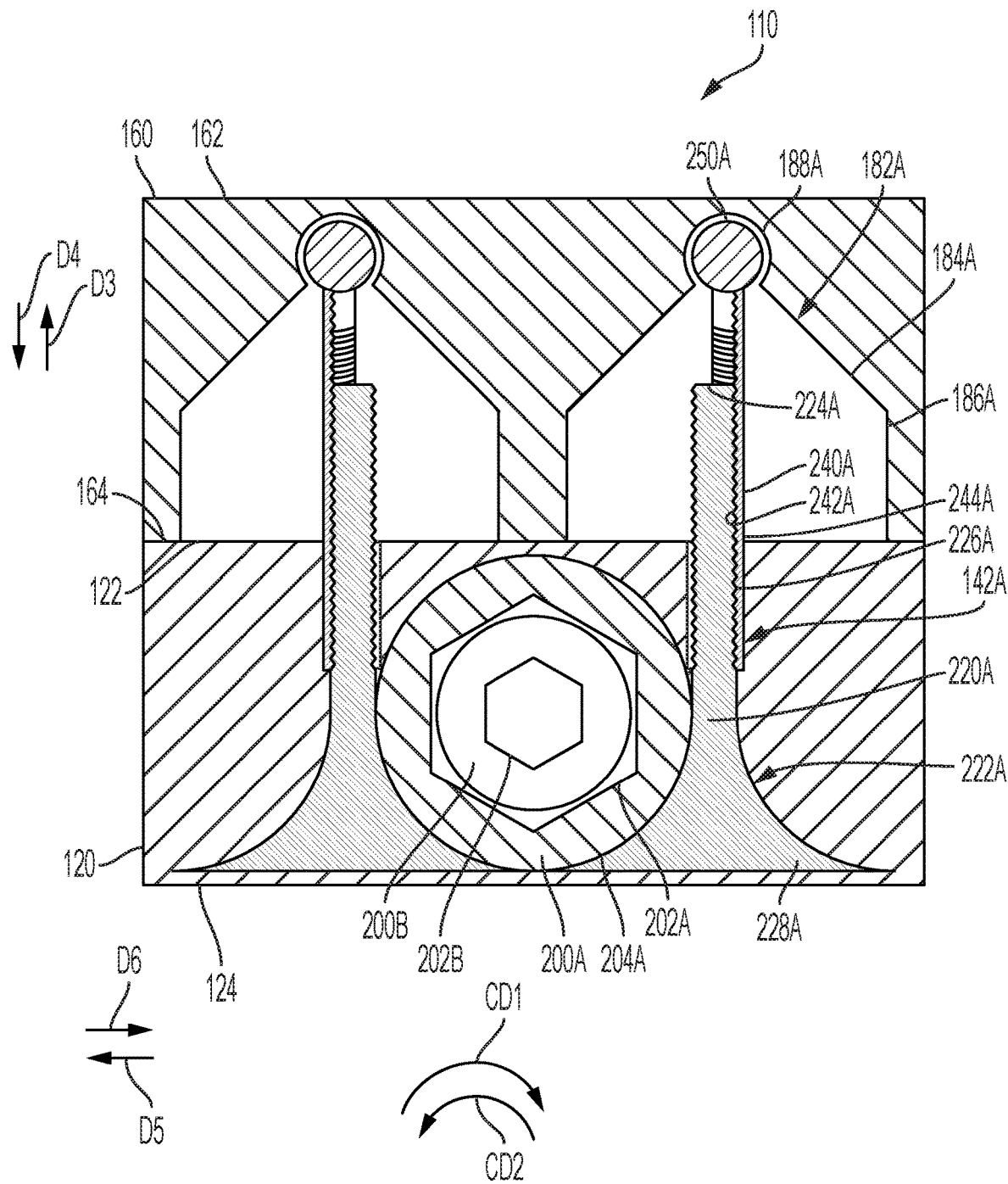
FIG. 9 is a cross-sectional view of the expandable intervertebral fusion implant taken generally along line 9-9 in FIG. 7A.
Figure 10:
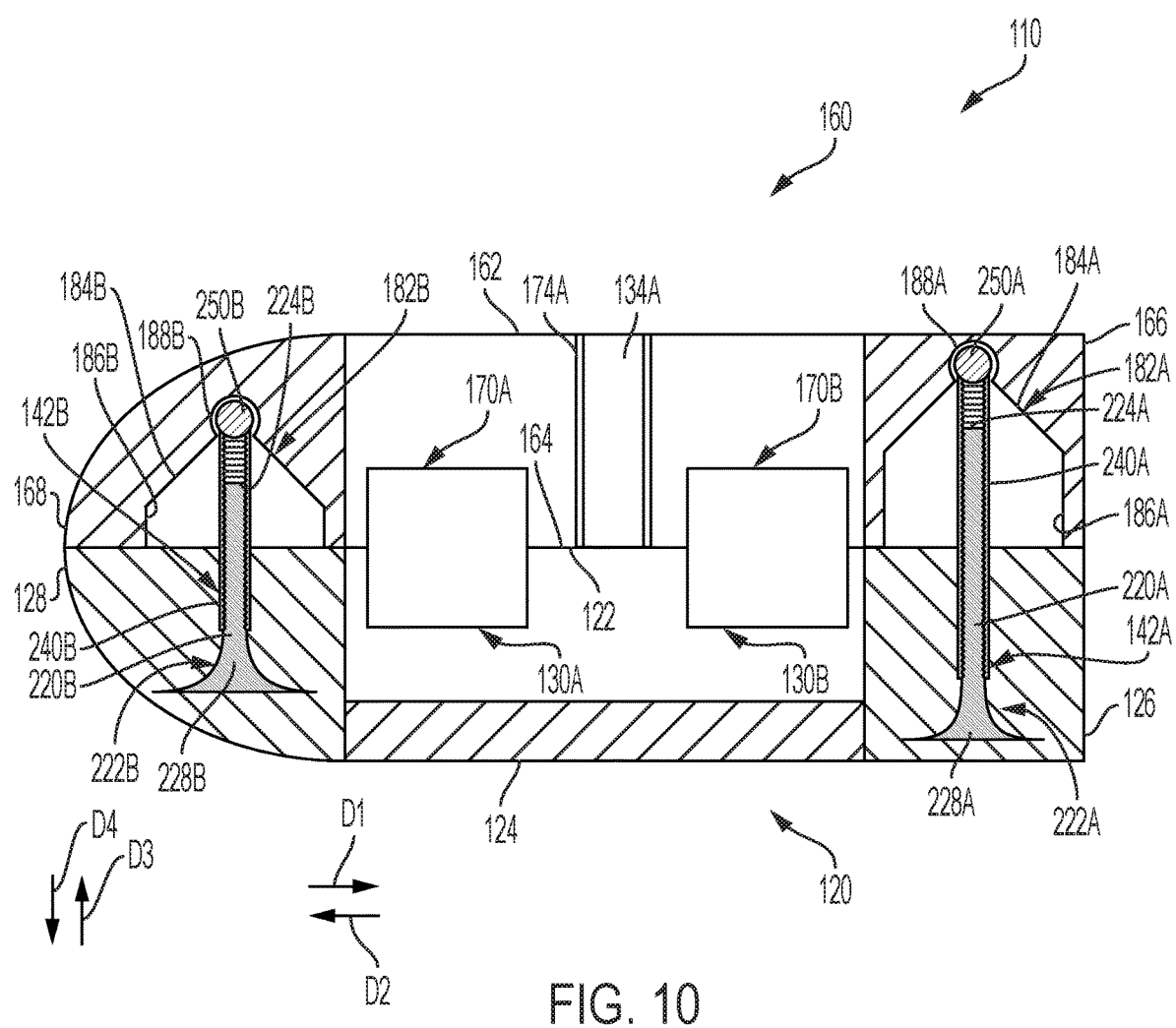
FIG. 10 is a cross-sectional view of the expandable intervertebral fusion implant taken generally along line 10-10 in FIG. 7A.

FIG. 7A is a front perspective view of expandable intervertebral fusion implant 110, in a collapsed state. FIG. 7B is a front perspective view of expandable intervertebral fusion implant 110, in an expanded state. FIG. 8 is a cross-sectional view of expandable intervertebral fusion implant 110 taken generally along line 8-8 in FIG. 7A. FIG. 9 is a cross-sectional view of expandable intervertebral fusion implant 110 taken generally along line 9-9 in FIG. 7A. FIG. 10 is a cross-sectional view of expandable intervertebral fusion implant 110 taken generally along line 10-10 in FIG. 7A. Expandable intervertebral fusion implant 110 generally comprises inferior component 120, superior component 160, and at least one expansion mechanism, for example, a worm drive comprising worm 200A and/or worm 200B and screw 220A and/or screw 220B, respectively. The following description should be read in view of FIGS. 7A-10.

Inferior component 120 comprises top surface 122, bottom surface 124, end 126, and end 128. Top surface 122 is an interior surface of expandable intervertebral fusion implant 110 that generally faces superior component 160 and is operatively arranged to engage and/or abut against surface 164. Bottom surface 124 is an exterior surface of expandable intervertebral fusion implant 110 that generally faces away from superior component 160 and is operatively arranged to engage and/or abut against a vertebra, as will be described in greater detail below. In some embodiments, surface 122 is arranged parallel to surface 124. In some embodiments, surface 122 is arranged nonparallel to surface 124. In some embodiments, surface 124 is curvilinear, for example, proximate end 128.

In some embodiments, inferior component 120 further comprises one or more holes. For example, inferior component 120 comprises hole 121A, which extends from end 126. Hole 121A extends from end 126 in direction D1 and is arranged to house worm 200A, as will be described in greater detail below. Inferior component 120 comprises hole 121B arranged proximate end 128. Hole 121B is arranged to house worm 200B, as will be described in greater detail below. In some embodiments, hole 121B is equal is size (e.g., diameter) to hole 121A. In some embodiments, hole 121B is not equal in size to hole 121A. Inferior component 120 comprises holes 130A and 130B, which extend through inferior component 120 in direction D5. Holes 130A-B extend from surface 122 in direction D4. Inferior component 120 comprises hole 132, which extends from surface 122 to surface 124. In some embodiments, hole 132 may instead be a plurality of holes, not just one. Holes 130A-B and 132 are operatively arranged to allow bone fusion material, which may be injected within expandable intervertebral fusion implant 110 once implanted within a spinal column, to engage adjacent vertebra thereby encouraging bony fusion. As such, it should be appreciated that any number of holes of any number of geometric shapes can be arranged in inferior component 120. Hole 121A is operatively arranged to allow for the injection of bone material. As will be described in greater detail below, worm 200A is arranged in hole 121A and comprises through-hole 202A. Once expandable intervertebral fusion implant 110 is implanted, bone material can be injected therein via hole 202A. Hole 121B may allow for fusion in some embodiments wherein worm 200B comprises a through-hole.

Inferior component 120 further comprises at least one section, for example section 134A and section 134B, which extends vertically from surface 122 in direction D3. Sections 134A and 134B are operatively arranged to slidingly and pivotably engage grooves 174A and 174B, respectively, to maintain alignment of inferior component 120 and superior component 160 in directions D1 and D2 while still allowing superior component 160 and inferior component 120 to pivot with respect to each other. In some embodiments, section 134A comprises a tongue or protrusion extending in direction D6 therefrom and section 134B comprises a tongue or protrusion extending in direction D5 therefrom (see FIG. 7A).

Inferior component 120 further comprises one or more holes, for example holes 142A and 142B. Hole 142A is generally arranged proximate end 126 and extends from surface 122 in direction D4. Hole 142A comprises a radially inward facing surface and engages screw 220A, as will be described in greater detail below. In some embodiments, hole 142A comprises notch 144A arranged proximate or at surface 122. Notch 144A is operatively arranged to engage with protrusion 244A to non-rotatably connect sleeve 240A and inferior component 120. In some embodiments, hole 142A comprises a cylindrical section that engages screw 220A and sleeve 240A and a tapered portion proximate surface 124 that engages bevel gear 228A (see FIGS. 9-10). Hole 142B is generally arranged proximate end 128 and extends from surface 122 in direction D4. Hole 142B comprises a radially inward facing surface and engages screw 220B, as will be described in greater detail below. In some embodiments, hole 142B comprises notch 144B arranged proximate or at surface 122. Notch 144B is operatively arranged to engage with protrusion 244B to non-rotatably connect sleeve 240B and inferior component 120. In some embodiments, hole 142B comprises a cylindrical section that engages screw 220B and sleeve 240B and a tapered portion proximate surface 124 that engages bevel gear 228B (see FIG. 10). It should be appreciated that in some embodiments, and as shown, inferior component 120 comprises two holes 142A arranged proximate end 126 to engage two screws 220A and two holes 142B arranged proximate end 128 to engage two screws 220B.

Superior component 160 comprises top surface 162, bottom surface 164, end 166, and end 168. Top surface 162 is an exterior surface of expandable intervertebral fusion implant 110 that generally faces away from inferior component 120 and is operatively arranged to engage and/or abut against a vertebra, as will be described in greater detail below. Bottom surface 164 is an interior surface of expandable intervertebral fusion implant 110 that generally faces inferior component 120 and is operatively arranged to engage and/or abut against surface 122, as will be described in greater detail below. In some embodiments, surface 162 is arranged parallel to surface 164. In some embodiments, surface 162 is arranged nonparallel to surface 164. In some embodiments, surface 162 is curvilinear, for example, proximate end 168.

In some embodiments, superior component 160 further comprises one or more holes. For example, superior component 160 comprises holes 170A and 170B, which extend through superior component 160 in direction D5. Holes 170A-B extend from surface 162 in direction D3. Superior component 160 comprises hole 172, which extends from surface 162 to surface 164. Holes 170A-B and 172 are operatively arranged to allow bone fusion material, which may be injected within expandable intervertebral fusion implant 110 once implanted within a spinal column, to engage adjacent vertebra thereby encouraging bony fusion. As such, it should be appreciated that any number of holes of any number of geometric shapes can be arranged in superior component 160. In some embodiments, superior component 160 further comprises one or more holes in end 166 and/or end 168.

Superior component 160 further comprises at least one groove, for example groove 174A and section 174B, which extends from surface 162 to surface 164. Grooves 174A and 174B are operatively arranged to slidingly and pivotably engage sections 134A and 134B, respectively, to maintain alignment of superior component 160 and inferior component 120 in directions D1 and D2 while still allowing superior component 160 and inferior component 120 to pivot with respect to each other. In some embodiments, groove 174A comprises an indentation or channel that is arranged to engage a tongue or protrusion of section 134A, and groove 174B comprises an indentation or channel that is arranged to engage a tongue or protrusion of section 134B. Such arrangement allows the tongue or protrusion of section 134A, 134B to engage the indentation or channel of groove 174A, 174B such that superior component 160 can displace in direction D3 and direction D4 relative to section 134A, 134B, but cannot displace in direction D5 and direction D6, or direction D1 or direction D2, relative to section 134A, 134B and thus inferior component 120.

Superior component 160 further comprises one or more holes, for example holes 182A and 182B. Hole 182A is generally arranged proximate end 166 and extends from surface 164 in direction D3. Hole 182A comprises surface 184A and surface 186A, and engages screw 220A and sleeve 240A, as will be described in greater detail below. In some embodiments, hole 182A further comprises socket 188A operatively arranged to pivotably connect to ball 250A of screw 220A and/or sleeve 240A. In some embodiments, surface 184A is frusto-conical and decreases in diameter in direction D3. Such an arrangement allows superior component 160 to pivot with respect to inferior component 120 such that, for example, end 168 can be expanded to a greater height than that of end 166, or vice versa. In some embodiments, surface 186A is cylindrical. Socket 188A is operatively arranged to engage ball 250A of screw 220A to expand and contract expandable intervertebral fusion implant 110. Hole 182B is generally arranged proximate end 168 and extends from surface 164 in direction D3. Hole 182B comprises surface 184B and surface 186B, and engages screw 220B and sleeve 240B, as will be described in greater detail below. In some embodiments, hole 182B further comprises socket 188B operatively arranged to pivotably connect to ball 250B of screw 220B and/or sleeve 240B. In some embodiments, surface 184B is frusto-conical and decreases in diameter in direction D3. Such an arrangement allows superior component 160 to pivot with respect to inferior component 120 such that, for example, end 168 can be expanded to a greater height than that of end 166, or vice versa. In some embodiments, surface 186B is cylindrical. Socket 188B is operatively arranged to engage ball 250B of screw 220B to expand and contract expandable intervertebral fusion implant 110.

Worm 200A is generally cylindrical and operatively arranged to rotatably engage hole 142A (or holes 142A), and specifically, screw 220A (or screws 220A). Worm 200A comprises through-hole 202A and radially outward facing surface 204A. Radially outward facing surface 204A comprises threading arranged to engage bevel gear 228A. Worm 200A is rotatably connected to inferior component 120 via hole 121A, meaning worm 200A is capable of displacing circumferentially with respect to inferior component 120. Worm 200A is not capable of displacing axially, in directions D1 and D2, with respect to inferior component 120. Through-hole 202A is operatively arranged to be engaged by a tool in order to rotate worm 200A, for example tool 300, as will be described in greater detail below. Such head may comprise any drive type suitable for rotating worm 200A, for example, Phillips and Frearson, slotted, combination, socked, internal hex, Allen, torx, external hex, etc. However, it should be appreciated that hole 202A is a through-hole that allows not only bone material to be injected into expandable intervertebral fusion implant 110, but also access to worm 200B. As worm 200A is rotated, for example in circumferential direction CD1 or circumferential direction CD2, threading of radially outward facing surface 204A engages teeth on bevel gear 228A to displace screw 220A in circumferential direction CD3 or circumferential direction CD4, within hole 142A.

Screw 220A comprises end 222A, 224A, and radially outward facing surface 226A. End 222A engages inferior component 120 and end 224A engages superior component 160. Radially outward facing surface 226A comprises threading operatively arranged to engage with threading of sleeve 240A, as will be described in greater detail below. Screw 220A further comprises bevel gear 228A connected to end 222A. As is known in the art, bevel gear 228A is operatively arranged to engage threading of radially outward facing surface 204A (of worm 200A). This engagement creates a worm drive, meaning that as worm 200A is rotated in circumferential direction CD1 or circumferential direction CD2, threading of radially outward facing surface 204A engages teeth on bevel gear 228A, which displaces screw 220A in circumferential direction CD3 or circumferential direction CD4 within hole 142A. In some embodiments, bevel gear 228A is fixedly secured to screw 220A. In some embodiments, bevel gear 228A and screw 220A are integrally formed.

Sleeve 240A is generally cylindrical, is rotatably connected to screw 220A at end 224A, and is connected to superior component 160. Sleeve 240A comprises radially inward facing surface 242A and protrusion or key 244A. Radially inward facing surface 242A comprises threading that engages threading on radially outward facing surface 226A of screw 220A. As previously described, protrusion 244A engages notch 144A in inferior component 120. As screw 220A is displaced in circumferential direction CD3 or circumferential direction CD4, as a result of worm 200A being displaced in circumferential direction CD1 or circumferential direction CD2, sleeve 240A displaces in direction D3 or direction D4 relative to screw 220A, thereby displacing superior component 160 in direction D3 and direction D4 relative to inferior component 120. In some embodiments, sleeve 240A comprises ball 250A operatively arranged to pivotably engage superior component 160, specifically, socket 188A. Such "ball and socket" joint connection allows for pivotable movement of superior component 160 relative to inferior component 120. In some embodiments, sleeve 240A only partially surrounds screw 220A. In some embodiments, sleeve 240A completely circumscribes screw 220A. Sleeve 240A may also protect screw 220A and hole 142A from ingrowth of foreign materials (e.g., tissue, bone fusion material, etc.).

Screw 220A and sleeve 240A are capable of displacing within hole 142A. Specifically, screw 220A is capable of displacing in circumferential directions CD3 and CD4 relative to inferior component 120 and sleeve 240A is capable of displacing in directions D3 and D4 relative to inferior component 120. The engagement of worm 200A and screw 220A (i.e., bevel gear 228A) operates similar to a worm drive, wherein rotational displacement of worm 200A causes rotational displacement of screw 220A and linear displacement of sleeve 240A. As such, when worm 200A is rotated in a first rotational direction, screw 220A is displaced within hole 142A such that sleeve 240A and superior component 160 are displaced in direction D3 relative to inferior component 120, expanding expandable intervertebral fusion implant 110. When worm 200A is rotated in a second rotational direction, opposite the first rotational direction, screw 220A is displaced within hole 142A such that sleeve 240A and superior component 160 are displaced in direction D4 relative to inferior component 120, contracting expandable intervertebral fusion implant 110. It should be appreciated that while the drawings illustrate only one worm 200A arranged to engage two screws 220A at the same time, in some embodiments expandable intervertebral fusion implant 110 may comprise two worms 200A that independently engage the two screws 220A. Such an arrangement would allow for each corner (of end 166) to be expanded/contracted independently of each other.

Worm 200B is generally cylindrical and operatively arranged to rotatably engage hole 142B (or holes 142B), and specifically, screw 220B (or screws 220B). Worm 200B comprises hole 202B and radially outward facing surface 204B. In some embodiments, hole 202B is a through-hole. In some embodiments, hole 202B is not a through-hole. Radially outward facing surface 204B comprises threading arranged to engage bevel gear 228B. Worm 200B is rotatably connected to inferior component 120 via hole 121B, meaning worm 200B is capable of displacing circumferentially with respect to inferior component 120. Worm 200A is not capable of displacing axially, in directions D1 and D2, with respect to inferior component 120. Hole 202B is operatively arranged to be engaged by a tool in order to rotate worm 200B, for example tool 300, as will be described in greater detail below. Such head may comprise any drive type suitable for rotating worm 200B, for example, Phillips and Frearson, slotted, combination, socked, internal hex, Allen, torx, external hex, etc. As worm 200B is rotated, for example in circumferential direction CD1 or circumferential direction CD2, threading of radially outward facing surface 204B engages teeth on bevel gear 228B to displace screw 220B in circumferential direction CD3 or circumferential direction CD4, within hole 142B.

Screw 220B comprises end 222B, 224B, and radially outward facing surface 226B. End 222B engages inferior component 120 and end 224B engages superior component 160. Radially outward facing surface 226B comprises threading operatively arranged to engage with threading of sleeve 240B, as will be described in greater detail below. Screw 220B further comprises bevel gear 228B connected to end 222B. As is known in the art, bevel gear 228B is operatively arranged to engage threading of radially outward facing surface 204B (of worm 200B). This engagement creates a worm drive, meaning that as worm 200B is rotated in circumferential direction CD1 or circumferential direction CD2, threading of radially outward facing surface 204B engages teeth on bevel gear 228B, which displaces screw 220B in circumferential direction CD3 or circumferential direction CD4 within hole 142B. In some embodiments, bevel gear 228B is fixedly secured to screw 220B. In some embodiments, bevel gear 228B and screw 220B are integrally formed.

Sleeve 240B is generally cylindrical, is rotatably connected to screw 220B at end 224B, and is connected to superior component 160. Sleeve 240B comprises radially inward facing surface 242B and protrusion or key 244B. Radially inward facing surface 242B comprises threading that engages threading on radially outward facing surface 226B of screw 220B. As previously described, protrusion 244B engages notch 144B in inferior component 120. As screw 220B is displaced in circumferential direction CD3 or circumferential direction CD4, as a result of worm 200B being displaced in circumferential direction CD1 or circumferential direction CD2, sleeve 240B displaces in direction D3 or direction D4 relative to screw 220B, thereby displacing superior component 160 in direction D3 and direction D4 relative to inferior component 120. In some embodiments, sleeve 240B comprises ball 250B operatively arranged to pivotably engage superior component 160, specifically, socket 188B. Such "ball and socket" joint connection allows for pivotable movement of superior component 160 relative to inferior component 120. In some embodiments, sleeve 240B only partially surrounds screw 220B. In some embodiments, sleeve 240B completely circumscribes screw 220B. Sleeve 240B may also protect screw 220B and hole 142B from ingrowth of foreign materials (e.g., tissue, bone fusion material, etc.).

Screw 220B and sleeve 240B are capable of displacing within hole 142B. Specifically, screw 220B is capable of displacing in circumferential directions CD3 and CD4 relative to inferior component 120 and sleeve 240B is capable of displacing in directions D3 and D4 relative to inferior component 120. The engagement of worm 200B and screw 220B (i.e., bevel gear 228B) operates similar to a worm drive, wherein rotational displacement of worm 200B causes rotational displacement of screw 220B and linear displacement of sleeve 240B. As such, when worm 200B is rotated in a first rotational direction, screw 220B is displaced within hole 142B such that sleeve 240B and superior component 160 are displaced in direction D3 relative to inferior component 120, expanding expandable intervertebral fusion implant 110. When worm 200B is rotated in a second rotational direction, opposite the first rotational direction, screw 220B is displaced within hole 142B such that sleeve 240B and superior component 160 are displaced in direction D4 relative to inferior component 120, contracting expandable intervertebral fusion implant 110. It should be appreciated that while the drawings illustrate only one worm 200B arranged to engage two screws 220B at the same time, in some embodiments expandable intervertebral fusion implant 110 may comprise two worms 200B that independently engage the two screws 220B. Such an arrangement would allow for each corner (of end 168) to be expanded/contracted independently of each other.

It should be appreciated that in some embodiments, expandable intervertebral implant 110 comprises one or more expansion mechanisms, for example, four worm drives and four screws. Specifically, and as shown, inferior component 120 comprises two worms, namely, worms 200A and 200B, and four screws, namely, screws 220A engaged with worm 200A and screws 220B engaged with worm 200B. The arrangement of the expansion mechanisms as well as the pivotable connection of the screws/sleeves to the superior component (i.e., the ball and socket joints) allows for a user to individually expand each end of expandable intervertebral implant 110 to the desired height. In other words, surface 162 need not be parallel to surface 124, which allows for a more custom expansion of expandable intervertebral implant 110. Furthermore, and as previously described, in some embodiments, each of the four screws comprises its own worm. In such embodiments, a user can individually expand each corner of expandable intervertebral implant 110 to the desired height.

Figure 11:
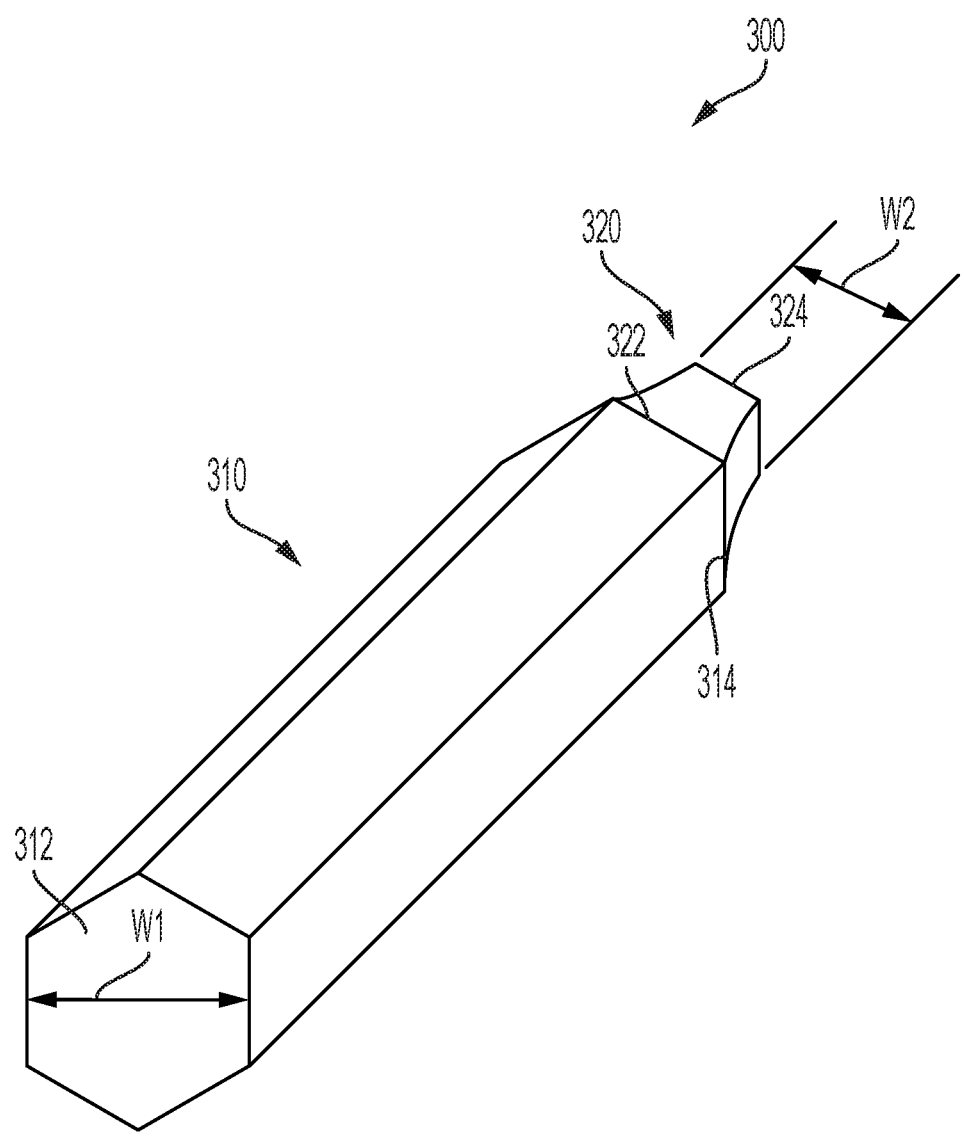
FIG. 11 is a perspective view of a tool used for expanding and collapsing the expandable intervertebral fusion implant shown in FIG. 7A; and, FIG. 12 is an anterior perspective view of a spinal column including the expandable intervertebral fusion implant shown in FIG. 7A, in an expanded state.

FIG. 11 is a perspective view of tool 300 used for expanding and collapsing expandable intervertebral fusion implant 110. Tool 300 comprises section 310 and section 320. Section 310 comprises proximal end 312 and distal end 322. Section 320 is connected to distal end 322 of section 310 and comprises end 322 and end 324. Section 312 is hexagonal (i.e., an Allen wrench) and comprises width W1. Width W1 is measured across-flats (AF), which is the distance between two opposite parallel flat sides of the key. Section 320 is hexagonal and end 324 comprises width W2. Width W2 is measured AF. In some embodiments, width W2 is less than width W1. In some embodiments, width W2 is equal to width W1. As best shown in FIG. 8, tool 300 is operatively arranged to engage both worm 200A and worm 200B at the same time. Width W1 corresponds to width W3 of hole 202A of worm 200A. Width W3 is measured AF. Thus, when section 310 is engaged with hole 202A, tool 300 and worm 200A are non-rotatably connected. Width W2 corresponds to width W4 of hole 202B of worm 200B. Width W4 is measured AF. Thus, when section 320 is engaged with hole 202B, tool 300 and worm 200B are non-rotatably connected. It should be appreciated that tool 300 is only one example of a tool that can be used to expand and contract expandable intervertebral fusion implant 110, and that any tool suitable for rotating worm 200A and worm 200B, either at the same time or independently of each other, may be used. In some embodiments, worm 200A and worm 200B are rotated at different times (independently) or at different rates in order to achieve a non-parallel state of expandable intervertebral fusion implant 110 (i.e., surface 162 is non-parallel to surface 124).

Figure 12:
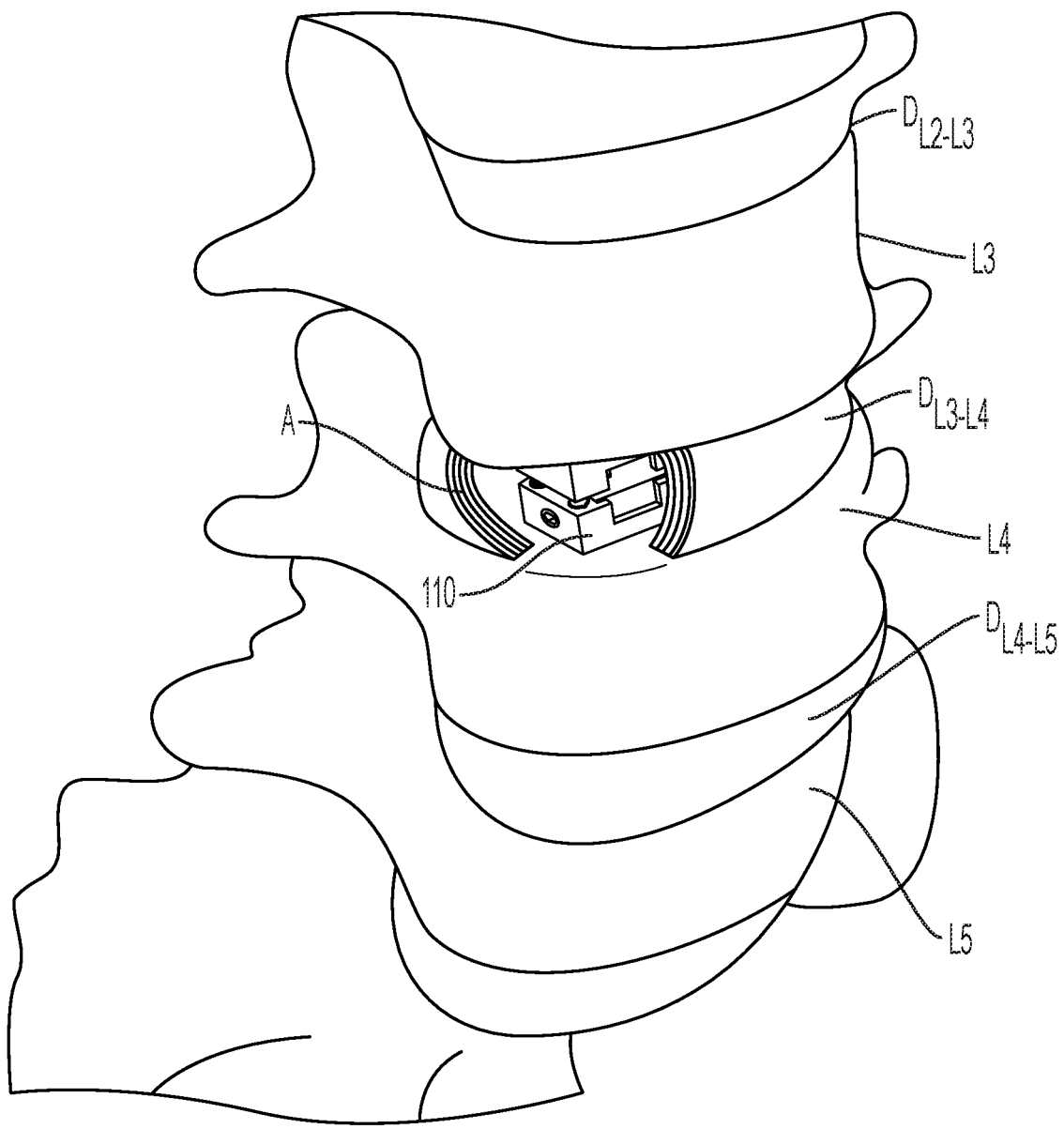

FIG. 12 is an anterior perspective view of a spinal column including expandable intervertebral fusion implant 110, in an expanded state. Expandable intervertebral fusion implant 110 is inserted into the spinal column between, for example, vertebra L3 and vertebra L4, or where disc $D_{L3-L4}$ should be. Expandable intervertebral fusion implant 110 is then vertically expanded until the desired height is reached. As previously described, expandable intervertebral implant 110 is expanded by rotating worm 200A and/or worm 200B. It should be appreciated that expandable intervertebral implant 110 may be expanded prior to insertion, or after insertion. Expandable intervertebral implant 110 is then filled with fusion material, for example, via hole 202A in worm 200A, and left in situ.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
110 Expandable intervertebral fusion implant
120 Inferior component
121A Hole
121B Hole
122 Surface
124 Surface
126 End
128 End
130A Hole
130B Hole
132 Hole
134A Section
134B Section
142A Hole
142B Hole
144A Notch
144B Notch
160 Superior component
162 Surface
164 Surface
166 End
168 End
170A Hole
170B Hole
172 Hole
174A Groove
174B Groove
182A Hole
182B Hole
184A Surface
184B Surface
186A Surface
186B Surface
188A Socket
188B Socket
200A Worm
200B Worm
202A Hole
202B Hole
204A Radially outward facing surface
204B Radially outward facing surface 220A Screw
220B Screw
222A End
222B End
224A End
224B End
226A Radially outward facing surface
226B Radially outward facing surface
228A Bevel gear
228B Bevel gear
240A Sleeve
240B Sleeve
242A Radially inward facing surface
242B Radially inward facing surface
244A Protrusion
244B Protrusion
250A Ball
250B Ball
300 Tool
310 Section
312 End
314 End
320 Section
322 End
324 End
CD1 Circumferential direction
CD2 Circumferential direction
CD3 Circumferential direction
CD4 Circumferential direction
D1 Direction
D2 Direction
D3 Direction
D4 Direction
D5 Direction
D6 Direction
W1 Width
W2 Width
W3 Width
W4 Width

What is claimed is:

1. An expandable intervertebral fusion implant, comprising:
an inferior component, including:
a first top surface;
a first bottom surface;
a first end including a first worm rotatably arranged therein, the first worm comprising a through-hole operatively arranged to allow material to be injected therethrough and into a central hole of expandable intervertebral fusion implant; and,
a second end including a second worm rotatably arranged therein;
a superior component, including:
a second top surface;
a second bottom surface;
a third end; and,
a fourth end;
a section extending from one of the inferior component and the superior component and a groove arranged in the other of the inferior component and the superior component, the section being engaged with the groove; and,
a first expansion mechanism including a first screw, the first screw comprising a first bottom end connected to the inferior component and a first top end connected to the superior component;
wherein as the first worm is rotated in a first circumferential direction, the first screw rotates in a second circumferential direction and the superior component is displaced relative to the inferior component.

2. The expandable intervertebral fusion implant as recited in claim 1, wherein:
the first worm comprises a radially outward facing surface comprising threading; and,
the first expansion mechanism further comprises a first bevel gear engaged with the threading.

3. The expandable intervertebral fusion implant as recited in claim 2, wherein the first expansion mechanism further comprises a first sleeve threadably engaged with the first worm.

4. The expandable intervertebral fusion implant as recited in claim 3, wherein as the first screw rotates in the second circumferential direction, the first sleeve displaces away from the inferior component.

5. The expandable intervertebral fusion implant as recited in claim 3, wherein the first sleeve is pivotably connected to the superior component.

6. The expandable intervertebral fusion implant as recited in claim 5, wherein:
the superior component further comprises a frusto-conical hole extending from the second bottom surface; and,
the first sleeve engages the frusto-conical hole.

7. The expandable intervertebral fusion implant as recited in claim 1, wherein the second worm is spaced apart from the first worm.

8. The expandable intervertebral fusion implant as recited in claim 1, further comprising a second expansion mechanism including a second screw, the second screw comprising a second bottom end connected to the inferior component and a second top end connected to the superior component.

9. The expandable intervertebral fusion implant as recited in claim 8, wherein as the second worm is rotated in the first circumferential direction, the second screw rotates in the second circumferential direction and the superior component is displaced relative to the inferior component.

10. The expandable intervertebral fusion implant as recited in claim 1, wherein the first worm and the second worm are concentrically aligned.

11. The expandable intervertebral fusion implant as recited in claim 1, wherein:
the first bottom surface is arranged to engage a first vertebra of a spine; and,
the second top surface is arranged to engage a second vertebra of a spine.

12. An expandable intervertebral fusion implant, comprising:
an inferior component, including:
a first top surface;
a first bottom surface;
a first end including a first worm rotatably arranged therein, the first worm comprising a through-hole forming a passageway for material to be injected into a central hole of the expandable intervertebral fusion implant and a radially outward facing surface comprising threading; and,
a second end including a second worm rotatably arranged therein, the second worm being space apart from and concentrically aligned with the first worm;
a superior component, including:
a second top surface;
a second bottom surface;
a third end; and,
a fourth end;

a first expansion mechanism including a first screw, the first screw comprising a first bottom end connected to the inferior component and a first top end connected to the superior component, the first expansion mechanism further including a first bevel gear arranged at the first bottom end and engaged with the threading; and, a second expansion mechanism including a second screw, the second screw comprising a second bottom end connected to the inferior component and a second top end connected to the superior component;

wherein:

as the first worm is rotated in a first circumferential direction, the first screw rotates in a second circumferential direction and the superior component is displaced relative to the inferior component; and, as the second worm is rotated in the first circumferential direction, the second screw rotates in the second circumferential direction and the superior component is displaced relative to the inferior component.

13. The expandable intervertebral fusion implant as recited in claim 12, wherein:

the first expansion mechanism further comprises a first sleeve threadably engaged with the first worm; and, as the first screw rotates in the second circumferential direction, the first sleeve displaces away from the inferior component.

14. The expandable intervertebral fusion implant as recited in claim 12, wherein the first top end is pivotably connected to the superior component.

15. The expandable intervertebral fusion implant as recited in claim 14, wherein:

the superior component further comprises a frusto-conical hole extending from the second bottom surface; and, the first screw engages the frusto-conical hole.

16. The expandable intervertebral fusion implant as recited in claim 12, wherein:

the first bottom surface is arranged to engage a first vertebra of a spine; and, the second top surface is arranged to engage a second vertebra of a spine.

\* \* \* \* \*